US011359178B2

(12) United States Patent
Takayama et al.

(10) Patent No.: US 11,359,178 B2
(45) Date of Patent: Jun. 14, 2022

(54) METHOD FOR PRODUCING PARASYMPATHETIC NEURONS

(71) Applicant: NATIONAL INSTITUTE OF ADVANCED INDUSTRIAL SCIENCE AND TECHNOLOGY, Tokyo (JP)

(72) Inventors: Yuzo Takayama, Tsukuba (JP); Yasuyuki Kida, Tsukuba (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 17/268,234

(22) PCT Filed: Aug. 23, 2019

(86) PCT No.: PCT/JP2019/033019
§ 371 (c)(1),
(2) Date: Feb. 12, 2021

(87) PCT Pub. No.: WO2020/040286
PCT Pub. Date: Feb. 27, 2020

(65) Prior Publication Data
US 2021/0171905 A1 Jun. 10, 2021

(30) Foreign Application Priority Data
Aug. 24, 2018 (JP) .............................. JP2018-157466

(51) Int. Cl.
*C12N 5/0793* (2010.01)
(52) U.S. Cl.
CPC ........ *C12N 5/0619* (2013.01); *C12N 2500/38* (2013.01); *C12N 2501/155* (2013.01); *C12N 2501/41* (2013.01); *C12N 2501/415* (2013.01)
(58) Field of Classification Search
CPC .................. C12N 5/0619; C12N 2501/155
See application file for complete search history.

(56) References Cited

U.S. PATENT DOCUMENTS

2007/0020608 A1    1/2007   Eriksson et al.
2018/0155682 A1    6/2018   Kida et al.

FOREIGN PATENT DOCUMENTS

WO    2016194522 A1    12/2016
WO    2018218193 A1    11/2018

OTHER PUBLICATIONS

Maden. Retinoic acid in the development, regeneration and maintenance of the nervous system 2008. Nat Rev Neurosci. 8(10)755-65 (Year: 2008).*
Benko et al. Phorbol-ester mediated suppression of hASH 1 synthesis: multiple ways to keep the level down 2011. Front. Mol. Neurosci. 4(1): 1-11 (Year: 2011).*
Written Opinion corresponding to PCT/JP2019/033019; dated Nov. 12, 2019 (16 pages, including English Translation).
International Search Report corresponding to PCT/JP2019/033019; dated Nov. 12, 2019 (2 pages, with English translation).
Berrard, S., et al., "Retinoic Acid Induces Cholinergic Differentiation of Cultured Newborn Rat Sympathetic Neurons", Journal of Neuroscience Research, 35(4), 1993, 382-389.
Mizuno, Kenichi , et al., "Intracellular factors involved in cholinergic neuronal differentiation", Bulletin of the Japanese Neurchemical Society, 28(1), 1989, 86-87. English abstract.
Takayama, Yuzo , et al., "Brief exposure to small molecules allows induction of mouse embryonic fibroblasts into neural crest-like precursors", FEBS Letter, 591(4), 2017, 590-602.
Takayama, Yuzo , et al., "Differentiation of Neurons of the Autonomic Nervous System from Human Pluripotent Stem Cells", Lecture Proceedings of the 2017 Annual Conference of Electronics, Information and Systems of the Institute of Electrical Engineers of Japan, 2017, 223-228. English abstract.
Extended European Search Report corresponding to EP 19852399. 5; dated Aug. 31, 2021 (8 pages).
Fukuta, Makoto , et al., "Derivation of Mesenchymal Stromal Cells from Pluripotent Stem Cells through a Neural Crest Lineage using Small Molecule Compounds with Defined Media", PLOS One 9(12):e112291, 2014, 1-25.
Kobayashi, Miqako , et al., "Cholinergic differentiation of cultured sympathetic neurons induced by retinoic acid", FEBS Letters 337(3), 1994, 259-264.
Mizuseki, Kenji, et al., "Generation of neural crest-derived peripheral neurons and floor plate cells from mouse and primate embryonic stem cells", PNAS 100(10), 2003, 5828-5833.
Nonaka, Daisuke , et al., "A Study of Gata3 and Phox2b Expression in Tumors of the Autonomic Nervous System", The American Journal of Surgical Pathology 37(8), 2013, 1236-1241.
Oh, Yohan , et al., "Functional Coupling with Cardiac Muscle Promotes Maturation of hPSC-Derived Sympathetic Neurons", Cell Stem Cell 19, 2016, 95-106.
Yamashita, Masakatsu , et al., "Identification of a Conserved GATA3 Response Element Upstream Proximal from the Interleukin-13 Gene Locus", The Journal of Biological Chemistry 277(44), 2002, p. 42399-42408.
Ersvaer, Elisabeth , et al., "The Protein Kinase C Agonist PEP005 (Ingenol 3-Angelate) in the Treatment of Human Cancer: A Balance between Efficacy and Toxicity", Toxins, 2(1), 2010, 174-194.
Goel, Gunjan , et al., "Phorbol Esters: Structure, Biological Activity, and Toxicity in Animals", International Journal of Toxicology, 26(4), 2007, 279-288.

(Continued)

*Primary Examiner* — Taeyoon Kim
*Assistant Examiner* — Alexandra F Connors
(74) *Attorney, Agent, or Firm* — Myers Bigel, P.A.

(57) ABSTRACT

The present invention provides a method for producing parasympathetic neurons from neural crest cells or autonomic neural progenitor cells derived therefrom, comprising a step of culturing the neural crest cells or autonomic neural progenitor cells derived therefrom in the presence of a cAMP production promoter, a BDNF signaling pathway activator, a GDNF signaling pathway activator, an NGF signaling pathway activator, an NT-3 signaling pathway activator, vitamin C, a protein kinase C activator, and a retinoic acid receptor agonist.

7 Claims, 8 Drawing Sheets

(56) References Cited

OTHER PUBLICATIONS

Hashimoto, Yuichi , "Retinobenzoic acids and nuclear retinoic acid receptors", Cell Structure and Function, 16(2), 1991, 113-123.

Howard, Marthe J., "Mechanisms and perspectives on differentiation of autonomic neurons", Developmental Biology, 277(2), 2005, 271-286.

Petros, Timothy J., et al., "Pluripotent stem cells for the study of CNS development", Frontiers in Molecular Neuroscience, 4(30), 2011, 1-12.

Shoba, T., et al., "Retinoic acid influences Phox2 expression of cardiac ganglionic cells in the developing rat heart", Neuroscience Letters, 321(1-2), 2002, 41-44.

\* cited by examiner

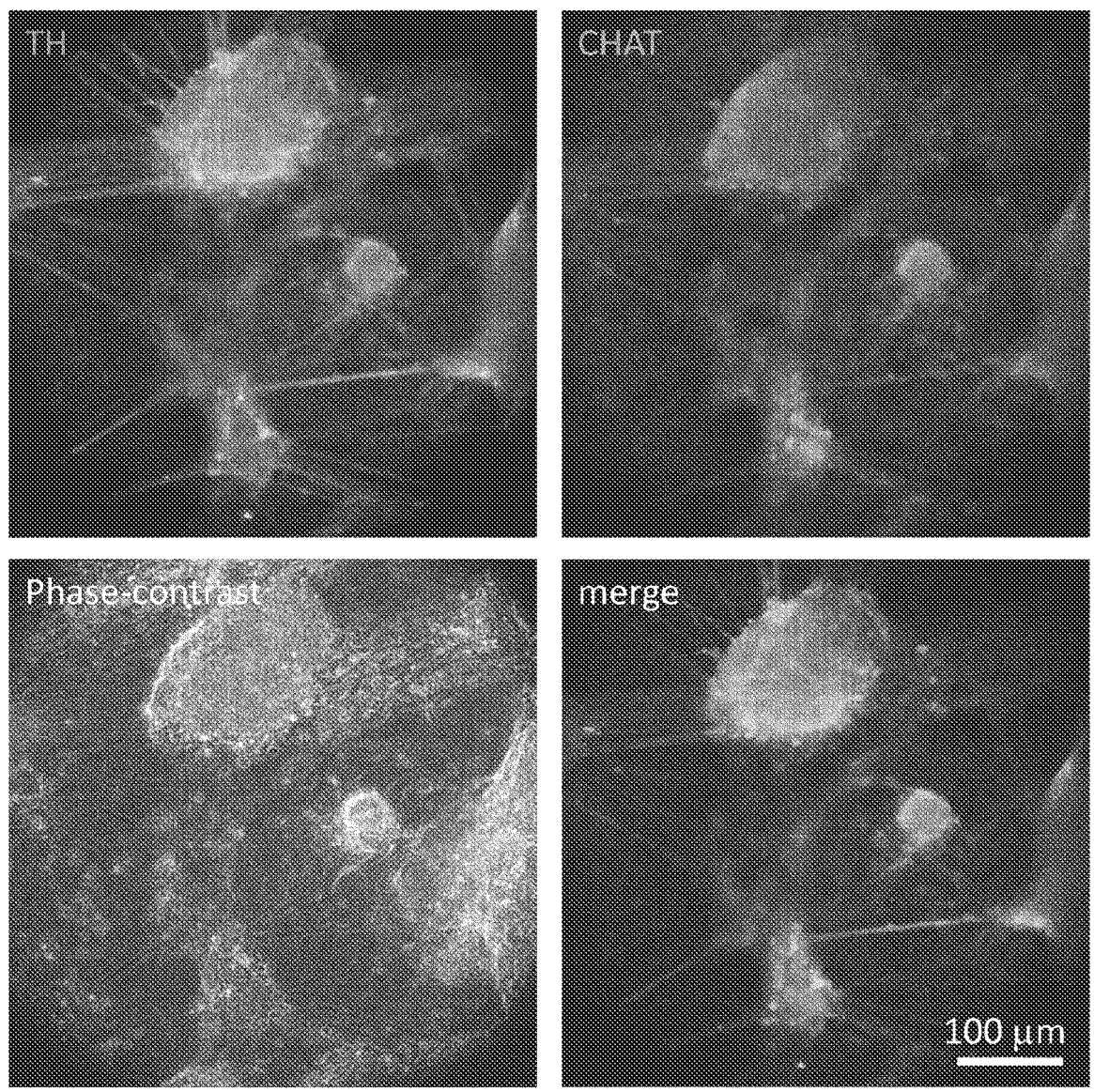

METHOD FOR PRODUCING PARASYMPATHETIC NEURONS

RELATED APPLICATIONS

This application is a 35 U.S.C. § 371 national stage application of PCT Application No. PCT/JP2019/033019, filed on Aug. 23, 2019, which claims priority from Japanese Patent Application No. 2018-157466, filed on Aug. 24, 2018, the contents of which are incorporated herein by reference in their entireties. The above-referenced PCT International Application was published in the Japanese language as International Publication No. WO 2020/040286 A1 on Feb. 27, 2020.

TECHNICAL FIELD

The present invention relates to a method for producing parasympathetic neurons. In particular, the present invention relates to a method for producing parasympathetic neurons from autonomic neural progenitor cells or neural crest cells.

BACKGROUND ART

Autonomic nerves are a part of the peripheral nervous system, form a neural pathway connecting the central nervous system and organs, and play an important role in regulation of body functions. Therefore, the loss or dysfunction of autonomic neurons leads to malfunction of organs. With the establishment of iPS cells, drug discovery support and cell transplantation treatment using human cells are progressing; however, a culture of a single type of cells derived from an organ or tissue is insufficient as a material used for such studies. There is a demand for in vitro models of the autonomic nervous system, which is responsible for regulating functions, in addition to sustentacular cells and the extracellular matrix, which form an organ or tissue and the vascular system serving as a supply route to an organ or tissue.

The inventors have been developing techniques to efficiently induce autonomic nerves from human pluripotent stem cells and have already reported a method for selectively inducing sympathetic neurons or parasympathetic neurons (e.g., Patent Document 1). However, when parasympathetic neurons are prepared by this method, autonomic neural progenitor cells need to be seeded at low density because progenitor cells seeded at high density differentiate into sympathetic neurons, and thus, there has been a problem that parasympathetic neurons can be obtained only with low efficiency. Improving of induction efficiency is therefore imperative to prepare parasympathetic neurons to be used in compound screening or cell transplantation.

CITATION LIST

Patent Document

[Patent Document 1] WO 2016/194522

SUMMARY OF INVENTION

Technical Problem

To address the above-described problem, the present invention provides a method for producing parasympathetic neurons from neural crest cells or autonomic neural progenitor cells derived therefrom with higher efficiency. Because neurotrophic factors are expensive, the inventors explored low molecular weight compounds that are inexpensive and can improve the efficiency of differentiation into parasympathetic neurons.

Solution to Problem

Phorbol 12-myristate 13-acetate (PMA) is a protein kinase C (PKC) activator and is known to enhance the expression of a transcription factor GATA3, which is essential for regulation of Th2 cell differentiation (M. Yamashita et al., "Identification of a conserved GATA3 response element upstream proximal from the Interleukin-13 gene locus", The Journal of Biological Chemistry, vol. 277, pp. 42399-42408, 2002). GATA3 is expressed in a variety of cells in addition to immune cells and has also been shown to be expressed in tumor cells in the autonomic nervous system (D. Nonaka et al., "A study of Gata3 and Phox2b expression in tumors of the autonomic nervous system", The American Journal of Surgical Pathology, vol. 37, pp. 1236-1241, 2013). However, the association between GATA3 and induction of differentiation into sympathetic/parasympathetic neurons is unknown thus far.

Retinoic acid (RA) has been shown to reduce the expression level of a marker of sympathetic neurons, tyrosine hydroxylase (TH), and enhance the expression of a marker of parasympathetic neurons, choline acetyltransferase (ChAT), in cultured rat sympathetic neurons (M. Kobayashi et al., "Cholinergic differentiation of cultured sympathetic neurons induced by retinoic acid. Induction of choline acetyltransferase-mRNA and suppression of tyrosine hydroxylase-mRNA levels", FEBS Letters, vol. 337, pp. 259-264, 1994). However, the effect of RA on induction of differentiation of undifferentiated autonomic neural progenitor cells into sympathetic/parasympathetic neurons has not been documented.

The inventors have diligently researched and, as a result, have found that parasympathetic neurons can be produced with high efficiency by further using a combination of PMA and RA in the abovementioned method for selectively inducing sympathetic/parasympathetic neurons, which has already been reported.

Specifically, an embodiment of the present invention provides a method for producing parasympathetic neurons from neural crest cells or autonomic neural progenitor cells derived therefrom, comprising a step of culturing the neural crest cells or autonomic neural progenitor cells derived therefrom in the presence of a cAMP production promoter, a BDNF signaling pathway activator, a GDNF signaling pathway activator, an NGF signaling pathway activator, an NT-3 signaling pathway activator, vitamin C, a protein kinase C activator, and a retinoic acid receptor agonist.

The protein kinase C activator is preferably a phorbol ester or an ingenol ester, more preferably phorbol 12-myristate 13-acetate.

The retinoic acid receptor agonist is preferably retinoic acid, tamibarotene, or Ch55, more preferably all-trans-retinoic acid.

The neural crest cells or autonomic neural progenitor cells derived therefrom are preferably cultured in the presence of a BMP signaling pathway activator, an SHH signaling pathway inhibitor, and a Wnt signaling pathway inhibitor before the step (a).

The BMP signaling pathway activator is preferably BMP2, BMP4, BMP7, or BMP2/4, the SHH signaling pathway inhibitor is preferably SANT-1, SANT-2, JK184, or jervine, and the Wnt signaling pathway inhibitor is preferably IWR-1, XAV939, or IWP-2.

The neural crest cells or autonomic neural progenitor cells derived therefrom are preferably seeded at a concentration of $2\times10^5$ to $5\times10^5$ cells/cm$^2$.

The neural crest cells or autonomic neural progenitor cells derived therefrom are preferably derived from a human.

The neural crest cells or autonomic neural progenitor cells derived therefrom are preferably differentiation-induced from pluripotent stem cells.

Furthermore, according to an embodiment, the present invention provides parasympathetic neurons obtained by the abovementioned method.

The parasympathetic neurons preferably express PHOX2B, ChAT, and MAP2.

Furthermore, according to an embodiment, the present invention provides a kit for preparing parasympathetic neurons from neural crest cells or autonomic neural progenitor cells derived therefrom, the kit comprising a cAMP production promoter, a BDNF signaling pathway activator, a GDNF signaling pathway activator, an NGF signaling pathway activator, an NT-3 signaling pathway activator, vitamin C, a protein kinase C activator, and a retinoic acid receptor agonist.

Advantageous Effects of Invention

According to the method of the present invention, parasympathetic neurons can be produced with high efficiency without an additional neurotrophic factor at a cost comparable to the cost in the reported method for selectively inducing parasympathetic neurons.

BRIEF DESCRIPTION OF DRAWINGS

FIG. 1 is a schematic diagram showing a known protocol to induce differentiation of pluripotent stem cell into sympathetic neurons and/or parasympathetic neurons.

FIG. 2 is a diagram showing microscopic images of cells obtained by culturing in a differentiation-inducing medium 4 (NDM only) to the 13th to 87th day from the start of culturing in accordance with the known protocol shown in FIG. 1 (upper left, stained TH; upper right, stained ChAT; lower right, an overlapped image of stained TH and ChAT; lower left, a microscopic phase contrast image).

DESCRIPTION OF EMBODIMENTS

Figure 3:
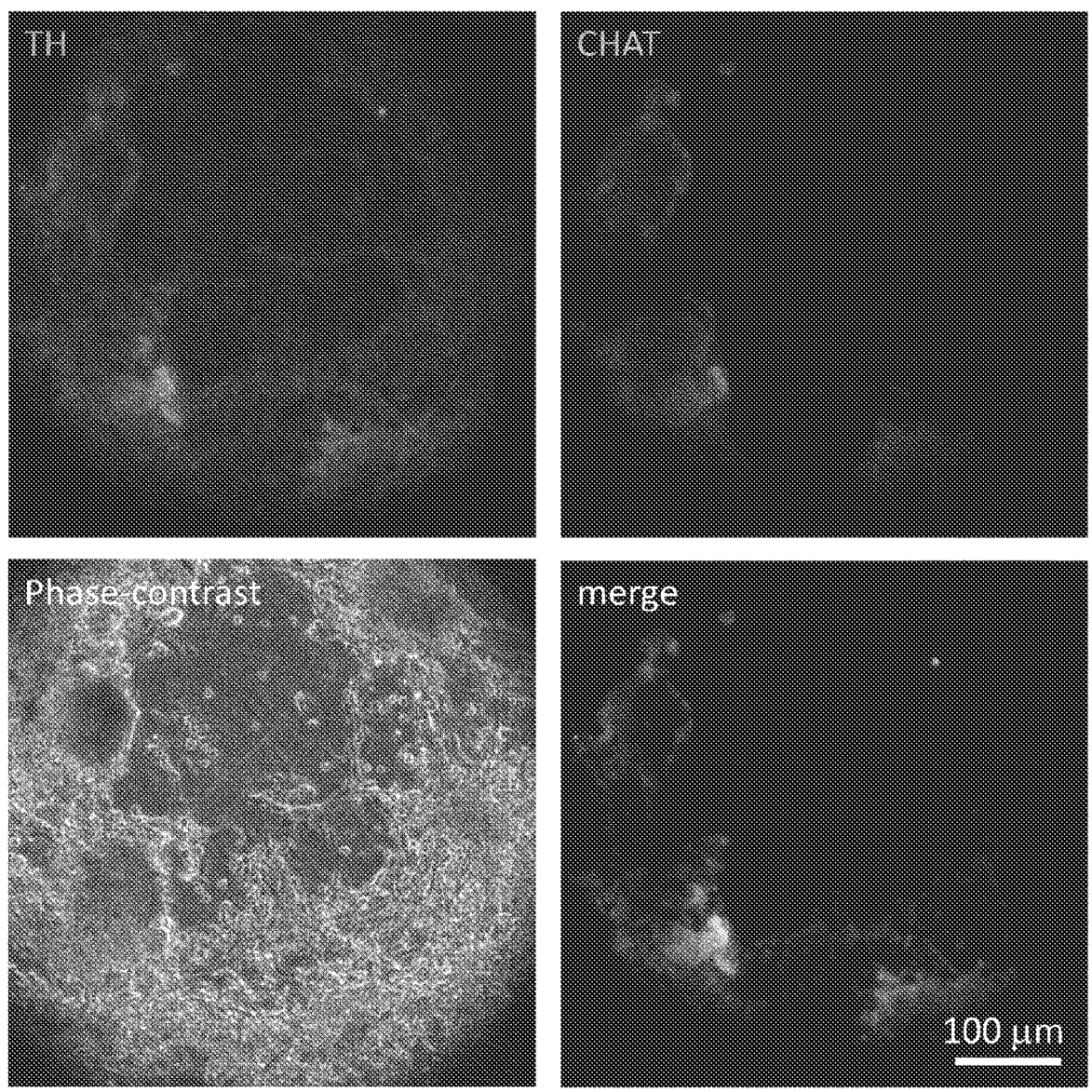
FIG. 3 is a diagram showing microscopic images of cells obtained by culturing in a differentiation-inducing medium 1 (NDM+PMA) to the 13th to 87th day from the start of culturing (upper left, stained TH; upper right, stained ChAT; lower right, an overlapped image of stained TH and ChAT; lower left, a microscopic phase contrast image).

The present invention will be described in detail below, but the scope of the present invention is not limited to the embodiments explained in the present specification.

According to a first embodiment, the present invention is a method for producing parasympathetic neurons from neural crest cells or autonomic neural progenitor cells derived therefrom, comprising (a) a step of culturing the neural crest cells or autonomic neural progenitor cells derived therefrom in the presence of a cAMP production promoter, a BDNF signaling pathway activator, a GDNF signaling pathway activator, an NGF signaling pathway activator, an NT-3 signaling pathway activator, vitamin C, a protein kinase C activator, and a retinoic acid receptor agonist (hereinafter also referred to as "differentiation induction step").

The "neural crest cells" are cells released from a neural crest tissue which is formed transiently in a vertebrate during early embryogenesis, and have the potential to differentiate into a variety of cells, such as Schwann cells, melanin cells, and cardiac muscle cells in addition to peripheral neurons including autonomic neurons. The neural crest cells that can be used in this embodiment may be derived from freely selected vertebrate animals, preferably derived from mammals such as mice, rats, guinea pigs, hamsters, rabbits, cats, dogs, sheep, pigs, cows, horses, goats, monkeys, or humans, in particular, preferably derived from humans.

The neural crest cells according to this embodiment can be isolated from the embryonic neural crest tissue. Of note, neural crests are classified into the cranial neural crest, vagal and sciatic neural crests, trunk neural crest, and cardiac neural crest, and neural crest cells derived from all of these crests have the potential to differentiate into autonomic neurons. These cells can be differentiated into autonomic neurons by the differentiation induction procedure as described below and can be used in this embodiment. Additionally, even in adults, neural crest-derived cells that are undifferentiated and maintain the same pluripotency as neural crest cells are present in neural crest cell-derived tissues such as bone marrow, heart, cornea, iris, dental pulp, and olfactory mucosa, and the neural crest-derived cells isolated from such adult tissues may be included in the neural crest cells according to this embodiment.

Alternatively, the neural crest cells according to this embodiment can be differentiation-induced from stem cells. The term "stem cell" used herein means a cell having a self-renewal potential and a differentiation potential. Stem cells are classified into totipotent stem cells, pluripotent stem cells, unipotent stem cells, and the like depending on the differentiation potential thereof. Any stem cells can be used in the method of this embodiment as long as they have at least the potential to differentiate into neural crest cells.

The neural crest cells according to this embodiment are preferably differentiation-induced from pluripotent stem cells. Examples of the pluripotent stem cells include embryonic stem (ES) cells, induced pluripotent stem (iPS) cells, embryonic germ (EG) cells, multipotent germline stem (mGS) cells, and Muse cells. Any pluripotent stem cells can be used in the method of this embodiment, but iPS cells or ES cells are preferred. Methods for preparing pluripotent stem cells have been well established (Practical protocol for culturing human pluripotent stem cells [second edition], 2010, Center for Developmental Biology, RIKEN, Japan). In accordance with a method known in this field, pluripotent stem cells can be prepared from cells isolated from the skin, blood, or the like and freely chosen cells such as established cell lines such as, for example, MRC-5 cells. Alternatively, established ES cell lines or iPS cell lines, obtained from, e.g., American Type Culture Collection (ATCC), may be used. Furthermore, pluripotent stem cells modified by genetic engineering techniques may also be used in the method of this embodiment.

Methods for inducing differentiation of pluripotent stem cells into neural crest cells have already been established (for example, WO 2016/194522; Oh et al., Cell Stem Cell, Vol. 19, pp. 95-106, 2016; and Fukuta et al., PLoS ONE, 9(12):e112291, 2014), and neural crest cells can be prepared by a method known in the field. Specifically, for example, neural crest cells are preferably prepared by culturing pluripotent stem cells using a DMEM/HAM's F-12 medium, a human embryonic stem (hES) cell medium, an N2 medium, a mixture thereof, or the like as a base medium and suitably adding a BMP signaling pathway inhibitor such as dorsomorphin (DM), a TGF signaling pathway inhibitor such as SB431542 (SB), a Wnt signaling pathway activator such as CHIR99021 (CHIR), an FGF signaling pathway activator such as bFGF, an epithelium growth factor (EGF) receptor (EGFR) signaling pathway activator such as an EGF, and the like. Additionally, pluripotent stem cells are preferably preconditioned by culturing using a medium containing a Rho kinase (ROCK) inhibitor such as Y-27632 for two to three days before differentiation induction (WO 2016/194522).

The "autonomic neural progenitor cell" according to this embodiment refers to a cell that is derived from a neural crest cell, and it is more likely to differentiate into an autonomic neuron than a neural crest cell, and it has the potential to differentiate into a sympathetic neuron and a parasympathetic neuron. The autonomic neural progenitor cell according to this embodiment can be defined based on expressions of both SOX10 and PHOX2B. The autonomic neural progenitor cells according to this embodiment can be prepared by a method in accordance with the above-described method for producing neural crest cells.

The neural crest cells or autonomic neural progenitor cells derived therefrom can be subcultured stably using a medium supplemented with EGF, basic fibroblast growth factor (bFGF), and the like, while maintaining the differentiating potential, until differentiation into parasympathetic neurons is induced (Fukuta et al., PLoS ONE, 9(12):e112291, 2014).

In the method of this embodiment, neural crest cells or autonomic neural progenitor cells derived therefrom are cultured in the presence of a cAMP production promoter, a BDNF signaling pathway activator, a GDNF signaling pathway activator, an NGF signaling pathway activator, an NT-3 signaling pathway activator, vitamin C, a protein kinase C activator, and a retinoic acid receptor agonist.

The "cAMP production promoter" according to this embodiment may be any known compound that promotes production of cyclic adenosine monophosphate (cAMP), and examples thereof include, but are not limited to, forskolin (FSK), L-858051, and dibutyryl cAMP (DB-cAMP). As the cAMP production promoter according to this embodiment, forskolin can be preferably used, and the concentration of forskolin in a medium can preferably be 5 to 50 µM.

The "BDNF signaling pathway activator" according to this embodiment may be any known compound that activates brain-derived neurotrophic factor (BDNF), its receptor TrkB, and a downstream signaling pathway thereof. As the BDNF signaling pathway activator according to this embodiment, BDNF can be preferably used, and the concentration of BDNF in a medium can preferably be 1 to 100 ng/mL.

The "GDNF signaling pathway activator" according to this embodiment may be any known compound that activates glia cell line derived neurotrophic factor (GDNF), its receptor GFRα, and a downstream signaling pathway thereof. As the GDNF signaling pathway activator according to this embodiment, GDNF can be preferably used, and the concentration of GDNF in a medium can preferably be 1 to 50 ng/mL.

The "NGF signaling pathway activator" according to this embodiment may be any known compound that activates nerve growth factor (NGF), its receptor TrkA, and a downstream signaling pathway thereof. As the NGF signaling pathway activator according to this embodiment, NGF-β can be preferably used, and the concentration of NGF-3 in a medium can preferably be 1 to 50 ng/mL.

The "NT-3 signaling pathway activator" according to this embodiment may be any known compound that activates neurotrophin-3 (NT-3), its receptor TrkC, and a downstream signaling pathway thereof. As the NT-3 signaling pathway activator according to this embodiment, NT-3 can be preferably used, and the concentration of NT-3 in a medium can preferably be 1 to 50 ng/mL.

The "vitamin C" according to this embodiment means ascorbic acid and a derivative thereof. The vitamin C according to this embodiment may be ascorbic acid, ascorbic acid 2-phosphate, a salt thereof, or a mixture thereof. As the vitamin C according to this embodiment, ascorbic acid can be preferably used, and the concentration of ascorbic acid in a medium can preferably be 10 to 100 µM.

The "protein kinase C activator" according to this embodiment may be any known compound that activates protein kinase C (PKC). Examples of the PKC activator according to this embodiment include phorbol esters such as phorbol 12-myristate 13-acetate (PMA) (also referred to as TPA), phorbol 12,13-dibutyrate (PDBu), 12-deoxyphorbol 13-acetate (prostratin), and phorbol 12,13-dihexanoate; ingenol esters such as ingenol 3-angelate (I3A) (also referred to as PEP005); bryostatin 1, bryostatin 2, DCP-LA (FR236924), (−)-Indolactam V, SC-9, SC-10, 1-oleoyl-2-acetylglycerol (OAG), 1-O-hexadecyl-2-O-arachidonyl-sn-glycerol, 1,2-dioctanoyl-sn-glycerol, phosphatidylinositol 4,5-bis phosphoric acid (PIP2), resiniferatoxin, mezerein, RHC-80267, and lipoxin A4. As the PKC activator according to this embodiment, a single compound or a combination of two or more compounds selected from these compounds can be used.

The PKC activator according to this embodiment is preferably a phorbol ester or an ingenol ester, in particular, preferably phorbol 12-myristate 13-acetate (PMA). The concentration of the PKC activator in a medium can be suitably determined. For example, when PMA is used, the concentration of PMA in a medium can preferably be 100 pg/mL to 10 µg/mL, more preferably 1 to 100 ng/mL, and in particular, preferably 1 to 50 ng/mL.

The "retinoic acid receptor agonist" according to this embodiment may be any known compound that can activate a retinoic acid receptor (RAR), and may be a retinoid or a compound that does not have a retinoid structure as long as it has an RAR agonist activity. Examples of the retinoid having the RAR agonist activity include retinoic acids such as all-transretinoic acid (ATRA) and 9-cis-retinoic acid (9cRA). Examples of the compound that has the RAR agonist activity and does not have a retinoid structure include tamibarotene (Am80), Ch55, TTNPB, and AM580. As the RAR agonist according to this embodiment, a single compound or a combination of two or more compounds selected from these compounds can be used.

The RAR agonist according to this embodiment is preferably retinoic acid, tamibarotene, or Ch55, more preferably retinoic acid, in particular, preferably all-transretinoic acid (ATRA). The concentration of the RAR agonist in a medium can be suitably determined. For example, when ATRA is used, the concentration of ATRA in a medium can be preferably 1 nM to 1 mM, more preferably 100 nM to 50 µM, in particular, preferably 500 nM to 10 µM.

The medium that can be used in the method of this embodiment can be prepared by using a DMEM/HAM's F-12 medium, an hES medium, an N2 medium, or a mixture thereof used in known methods (for example, Mizuseki et al., Proc. Natl. Acad. Sci. USA, 100:5828-5833 (2003); Fukuta et al., PLoS ONE 9(12):e112291 (2014); and WO 2016/194522) as a base medium and adding the abovementioned components. The differentiation induction step (a) in the method of this embodiment preferably uses an N2 medium as a base medium.

Additionally, the medium that can be used in the differentiation induction step (a) may further contain a CNTF signaling pathway activator optionally. The "CNTF signaling pathway activator" according to this embodiment may be any known compound that activates ciliary body neurotrophic factor (CNTF), its receptor CNTFR, and a downstream signaling pathway thereof. As the CNTF signaling pathway activator according to this embodiment, CNTF can preferably be used, and the concentration of CNTF in a medium can preferably be 1 to 100 ng/mL.

In the differentiation induction step (a) of this embodiment, neural crest cells or autonomic neural progenitor cells derived therefrom can be seeded at a concentration within a range of, for example, $5\times10^4$ to $5\times10^5$ cells/cm$^2$, preferably $2\times10^5$ to $5\times10^5$ cells/cm$^2$, more preferably $2.5\times10^5$ to $5\times10^5$ cells/cm$^2$. In the differentiation induction step (a) of this embodiment, neural crest cells or autonomic neural progenitor cells derived therefrom can be adherent-cultured. A plate that can be used for adherent culture is preferably coated with a single compound or a mixture of two or more compounds selected from extracellular substrates such as poly-L-ornithine, poly-D-lysine, laminin, fibronectin, and Matrigel. The culture conditions in the differentiation induction step (a) of this embodiment vary depending on the animal species from which cells are derived. For example, neural crest cells or autonomic neural progenitor cells derived therefrom that are derived from mammals are preferably cultured under conditions of 37° C. and 5% $CO_2$. The duration of the differentiation induction step (a) of this embodiment can be changed suitably depending on the intended maturity of parasympathetic neurons to be prepared. For example, the duration may be at least 20 days, 30 days, 50 days, 70 days, or longer, preferably 20 to 50 days, in particular, preferably 20 to 30 days.

The method of this embodiment may further comprise (b) a step of culturing neural crest cells or autonomic neural progenitor cells derived therefrom in the presence of a BMP signaling pathway activator, an SHH signaling pathway inhibitor, and a Wnt signaling pathway inhibitor (hereinafter, also referred to as "preconditioning step") before the differentiation induction step (a).

The "BMP signaling pathway activator" according to this embodiment may be any known compound that activates bone morphogenetic protein (BMP), its receptor (BMPR-I and/or BMPR-II), and a downstream signaling pathway thereof (e.g., Smad1, Smad5, Smad8) and may be a natural or modified BMP family protein. Examples of the BMP family protein include BMP2, BMP4, BMP7, and BMP2/4, and a single compound or a combination of two or more compounds selected from these compounds can be used as the BMP signaling pathway activator according to this embodiment.

The BMP signaling pathway activator according to this embodiment is preferably BMP4. The concentration of the BMP signaling pathway activator in a medium can be suitably determined. For example, when BMP4 is used, the concentration of BMP4 in a medium can be preferably 0.1 to 100 ng/mL, more preferably 5 to 50 ng/mL.

The "SHH signaling pathway inhibitor" according to this embodiment may be any known compound that inhibits a Sonic Hedgehog (SHH) signaling pathway, which comprises SHH, its receptor Patched (PTCH), its adjacent protein Smoothened (SMO), and a downstream glioma-associated oncogene (GLI) thereof. Examples of the SHH signaling pathway inhibitor according to this embodiment include SMO inhibitors such as SANT-1, SANT-2, and jervine and GLI inhibitors such as JK184, and a single compound or a combination of two or more compounds selected from these compounds can be used as the SHH signaling pathway inhibitor according to this embodiment.

The SHH signaling pathway inhibitor according to this embodiment is preferably SANT-1. The concentration of the SHH signaling pathway inhibitor in a medium can be suitably determined. For example, when SANT-1 is used, the concentration of SANT-1 in a medium can be preferably 20 nM to 2 µM, more preferably 100 to 500 nM.

The "Wnt signaling pathway inhibitor" according to this embodiment may be any known compound that inhibits a Wnt family protein, its receptor (e.g., a seven-pass transmembrane receptor Frizzled [Fz], single-pass transmembrane receptors low-density lipoprotein receptor-related proteins 5 and 6 [LRPS/6], orphan receptor tyrosine kinases 1 and 2 [Ror1/2], receptor type tyrosine kinase [Ryk]), or a downstream signaling pathway thereof (β-catenin pathway, planar cell polar [PCP] pathway, Ca' pathway), and a single compound or a combination of two or more compounds selected from these compounds can be used as the Wnt signaling pathway inhibitor according to this embodiment.

The Wnt signaling pathway inhibitor according to this embodiment is preferably a compound that inhibits Wnt-3a, its receptors Fz and LRPS/6, and a downstream β-catenin pathway thereof. Examples of such a compound include IWR compounds such as IWR-1 and IWP compounds such as XAV939 and IWP-2, in particular, preferably IWR-1. The concentration of the Wnt signaling pathway inhibitor in a medium can be suitably determined. For example, when IWR-1 is used, the concentration of IWR-1 in a medium can be preferably 0.5 to 100 µM, more preferably 2 to 20 µM.

The medium that can be used in the preconditioning step (b) according to this embodiment can be prepared using a base medium similar to the media that can be used in the differentiation culture step (a) defined above. A medium mixture of an hES medium and an N2 medium is preferably used as a base medium, and the mixing ratio thereof is preferably within a range of 1:3 to 3:1. The preconditioning step (b) according to this embodiment is performed by either adherent culturing or suspension culturing (see WO 2016/194522).

According to the method of this embodiment, parasympathetic neurons can be prepared with high efficiency even under a high density culturing conditions of $2 \times 10^5$ cells/cm$^2$ only by further using a combination of PMA and RA in the reported method for selectively inducing parasympathetic neurons. Of note, the efficiency for selective induction of differentiation into parasympathetic neurons can be assessed based on the ratio (ChAT/TH) of a parasympathetic neuron marker choline acetyltransferase (ChAT) and a sympathetic neuron marker tyrosine hydroxylase (TH). According to the method of this embodiment, parasympathetic neurons can be prepared with high efficiency in a ChAT/TH of 5 or higher, preferably 10 or higher.

According to a second embodiment, the present invention is parasympathetic neurons obtained by the above-described method. Whether cells obtained by the above-described method are parasympathetic neurons is preferably determined by expressions of PHOX2B, ChAT, and microtubule associated protein 2 (MAP2), and confirmation of presence of a nicotinic acetylcholine receptor is more preferred.

According to a third embodiment, the present invention is a kit for producing parasympathetic neurons from neural crest cells or autonomic neural progenitor cells derived therefrom, the kit comprising a cAMP production promoter, a BDNF signaling pathway activator, a GDNF signaling pathway activator, an NGF signaling pathway activator, an NT-3 signaling pathway activator, vitamin C, a protein kinase C activator, and a retinoic acid receptor agonist. In this embodiment, the "cAMP production promoter," "BDNF signaling pathway activator," "GDNF signaling pathway activator," "NGF signaling pathway activator," "NT-3 signaling pathway activator," "vitamin C," "protein kinase C activator," and "retinoic acid receptor agonist" are similar to those defined above.

The kit of this embodiment can contain the above-described reagents by selecting them appropriately. Additionally, the kit of this embodiment may further contain additional reagents such as a CNTF signaling pathway activator, reagents for preconditioning neural crest cells or autonomic neural progenitor cells derived therefrom (e.g., BMP signaling pathway activators, SHH signaling pathway inhibitors, Wnt signaling pathway inhibitors), a culture plate, a manual including a differentiation induction protocol, and the like, in addition to the above-described reagents.

EXAMPLES

The present invention will be further explained with the following examples. However, these examples are not intended to limit the scope of the present invention in any way.

Reagents

The information (reagent name, manufacture number, manufacturer, abbreviated name, etc.) of the reagents used in the following example is as follows:

mTeSR1-cGMP (Stemcell Technologies: ST-85850G)—mTeSR1
DMEM/Ham's F-12 (Wako: 048-29785)
DMEM (high-glucose) (Wako: 043-30085)—DMEM
Opti-MEM (Life Technologies: 31985-070)
Fetal Bovine Serum (made in Australia) (Wako: SFBS)—FBS
Knockout Serum Replacement (Life Technologies: 10828-028)—KSR
N2 Supplement with Transferrin (Apo) (Wako: 141-09041)—N2 supplement
MEM Non-Essential Amino Acids Solution (Wako: 139-15651)—NEAA
Monothioglycerol Solution (Wako: 195-15791)
Penicillin-Streptomycin Solution (Wako: 168-23191)—P/S
Brain Derived Neurotrophic Factor, Human, recombinant (Wako: 020-12913)—BDNF
Glial-cell Derived Neurotrophic Factor, Human, recombinant (Wako: 075-04153)—GDNF
Nerve Growth Factor-β, Human, recombinant (Wako: 141-07601)—NGF
Neurotrophin-3, Human, recombinant (Wako: 141-06643)—NT-3
L-Ascorbic Acid Phosphate Magnesium Salt n-Hydrate (Wako: 01319641)—Ascorbic Acid
Y-27632 (Wako: 253-00513)
Forskolin (Wako: 067-02191)—FSK
Dorsomorphin (Sigma-Aldrich: P5499-5MG)—DM
SB431542 hydrate (Sigma-Aldrich: S4317-5MG)—SB
CHIR99021 (Cayman Chemical Company: 13122)—CHIR
IWR-1 (Sigma-Aldrich: I0161-5MG)
SANT-1 (Sigma-Aldrich: S4572-5MG)
Bone Morphogenetic Protein 4 (truncated), Human, recombinant (Wako: 022-17071)—BMP-4
Fibroblast Growth Factor (basic) (basic FGF), Human, recombinant (Wako: 064-04541)—bFGF
iMatrix-511 (Nippi: 892002)
MPC polymer (NOF: Lipidure CM5206E)
Poly-L-ornithine hydrobromide (Sigma-Aldrich: P3655, 10 mg)—PLO
Laminin from Engelbreth-Holm-Swarm murine sarcoma basement membrane (Sigma-Aldrich: L2020, 1 mg)—Laminin
Phorbol 12-Myristate 13-Acetate (Wako: 162-23591)—PMA
Retinoic acid (Sigma-Aldrich: R2625, 50 mg)—RA
Accutase (Life Technologies: A11105-01)
TrypLE Express Enzyme (Life Technologies: 12604-013)
UltraPure Distilled Water (Life Technologies: 10977-015)—DW
D-PBS(-) (Wako: 045-29795)—PBS
Tris Buffer Powder, pH 7.4 (Takara Bio: T9153)
Hydrochloric Acid (Wako: 080-01066)
Albumin, from Bovine Serum (Wako: 017-23294)—BSA
Dimethyl Sulfoxide (Wako: 074-29353)—DMSO
Formaldehyde Solution (Wako: 064-00406)
10 w/v % Polyoxyethylene (20) Sorbitan Monolaurate Solution (Wako: 161-24801)—Tween 20
Block Ace Powder (DS Pharma Biomedical: UK-B80)
Can Get Signal (registered trademark) Immunostain Enhancer Solution A (Toyobo: NKB-501)

Anti-Tyrosine Hydroxylase antibody (rabbit polyclonal) (Merck Millipore: AB152)

Anti-Choline Acetyltransferase antibody (rabbit polyclonal) (Abcam: ab68779)

Anti-PHOX2B Antibody (mouse monoclonal) (Proteintech: 66254-1-1g)

Anti-PHOX2B antibody (rabbit monoclonal) (Abcam: ab183741)

Anti-MAP2 antibody (mouse monoclonal) (Abcam: ab11267)

Hoechst 33342 solution (Dojindo: 346-07951)

F(ab')2-Goat anti-Mouse IgG (H+L) Secondary Antibody, Alexa Fluor (registered trademark) 488 Conjugate (Life Technologies: A11017)—Alexa Fluor488

F(ab')2-Goat anti-Rabbit IgG (H+L) Secondary Antibody, Alexa Fluor (registered trademark) 555 Conjugate (Life Technologies: A21430)—Alexa Fluor555

Fluo-4 AM (Invitrogen: F14201, 10×50 μg)

(−)-Nicotine (Sigma-Aldrich: N3876-5ML)

Basal Media (i) Human Embryonic Stem (hES) Cell Medium

A DMEM/Ham's F-12 containing 20% KSR, 1% NEAA, 1% monothioglycerol solution, and 1% P/S was used as a human embryonic stem cell medium (hESM).

(ii) N2 Medium

A DMEM/Ham's F-12 containing 1% N2 supplement, 1% NEAA, and 1% P/S was used as an N2 medium.

Preparation of Stock Solutions

An FSK stock solution was prepared as a 10 mM stock solution using DMSO.

A DM stock solution was prepared as a 1 mM stock solution using DMSO.

An SB stock solution was prepared as a 10 mM stock solution using DMSO.

A CHIR stock solution was prepared as a 3 mM stock solution using DMSO.

An IWR-1 stock solution was prepared as a 10 mM stock solution using DMSO.

A SANT-1 stock solution was prepared as a 250 μM stock solution using DMSO.

A BMP4 stock solution was prepared as a 100 μg/mL stock solution using 4 mM hydrochloric acid solution supplemented with 0.1% BSA.

A bFGF stock solution was adjusted using 1 mM Tris buffer (pH 7.4) at 500 μg/mL and then prepared as a 10 μg/mL stock solution using DMEM.

BDNF, GDNF, NGF, and NT-3 stock solutions were prepared as 10 μg/mL stock solutions using PBS.

An Ascorbic Acid stock solution was prepared as a 50 mg/mL stock solution using PBS.

A Y-27632 stock solution was prepared as a 10 mM stock solution using Opti-MEM.

A PLO stock solution was prepared as a 1 mg/mL stock solution using DW.

A PMA stock solution was prepared as a 10 μg/mL stock solution using DMSO.

An RA stock solution was prepared as a 1 mM stock solution using DMSO.

1. Preparation of Autonomic Neural Progenitor Cells (1-1. Culture of iPS Cells)

Human iPS cells (201B7 strain) were obtained from RIKEN BioResource Center. 1.5 mL of PBS was added to each well of a six-well plate, followed by further addition of iMatrix-511 (Nippi: 892002) at 0.5 μg/cm$^2$, and coating treatment was performed for one hour. Then, the solution was removed from each well, followed by addition of 2 mL of mTeSR1, and a Y-27632 stock solution was further added at a final concentration of 10 μM. iPS cells were seeded at 4×10$^4$ to 1×10$^5$ cells/well (4×10$^2$ to 1×10$^4$ cells/cm$^2$), and culture was continued on the day following the seeding and after, while the medium was replaced with mTeSR1 not containing Y-27632 every day.

When iPS cells grew and became semiconfluent, the cells were subcultured by the following procedures. mTeSR1 was removed from each well, followed by addition of 1 mL of an Accutase solution heated at 37° C., and the mixture was incubated for five minutes. Subsequently, the Accutase solution in each well was blown on the culture surface with a pipette to exfoliate the human iPS cells, and exfoliated human iPS cells were collected in a centrifuge tube. 1 mL of PBS was further added to the well to collect the human iPS cells remaining in the well into the centrifuge tube. The mixture was centrifuged at 200×g for four minutes. The supernatant was removed, and 1 mL of mTeSR1 was added to suspend the human iPS cells. The cells were counted. After the concentration was adjusted, the cells were placed in a fresh six-well plate coated with iMatrix.

(1-2. Preparation of Autonomic Neural Progenitor Cells)

(i) Preconditioning of iPS Cells

Up to 300 μL of MPC polymer was added to each well of a six-well plate, and non-adhesive treatment was performed on the well surface by drying the well in a clean bench for one hour. Each well was washed with PBS, followed by addition of 2 mL of mTeSR1 containing 10 μM Y-27632, and iPS cells were seeded at 1×10$^6$ cells/well. Then, the cells were cultured for two to three days until cell aggregates were formed, while the medium was replaced with mTeSR1 containing 10 μM Y-27632 every day.

(ii) Preparation of Autonomic Neural Progenitor Cells iPS cells were differentiated into neural crest cells at Steps 1 to 3 below, and autonomic neural progenitor cells with regulated intracellular signals were further obtained by performing preconditioning treatment at Steps 4 and 5 below:

Step 1: The medium was replaced with hESM containing 2 μM DM, 10 μM SB, and 10 ng/mL bFGF (all final concentrations) and cultured for two days.

Step 2: The medium was replaced with hESM containing 3 μM CHIR, 20 μM SB, and 10 ng/mL bFGF (all final concentrations) and cultured for three days.

Step 3: The medium was replaced with an hESM:N2 (3:1) medium mixture containing 3 μM CHIR and 10 ng/mL bFGF (both final concentrations) and cultured for two days.

Step 4: The medium was replaced with an hESM:N2 (1:1) medium mixture containing 10 μM IWR-1, 250 nM SANT-1, 25 ng/mL BMP4, and 10 ng/mL bFGF (all final concentrations) and cultured for two days.

Step 5: The Medium was Replaced with an hESM:N2 (1:3) Medium Mixture Containing 10 μM IWR-1, 250 nM SANT-1, 25 ng/mL BMP4, and 10 ng/mL bFGF (all final concentrations) and cultured for three days, followed by replacement with a fresh same medium, and the medium was further cultured for one day.

2. Induction of Autonomic Neural Progenitor Cells to Differentiate into Parasympathetic Neurons A 24-well plate coated with poly-L-ornithine and laminin was prepared by the following procedure. The plate was coated for one hour with a PLO solution (20 μg/mL) prepared with DW, washed once with DW, and coated for two hours with a laminin solution (5 μg/mL) prepared with PBS. Subsequently, the N2 medium was supplemented with 10 μM FSK, 10 ng/mL BDNF, 10 ng/mL GDNF, 10 ng/mL NT-3, 10 ng/mL NGF, and 50 μg/mL Ascorbic Acid (all final concentrations) to prepare a neural differentiation medium (NDM).

The following four kinds of differentiation-inducing media were prepared using NDM:

Differentiation-inducing medium 1: NDM+10 ng/mL PMA (final concentration)

Differentiation-inducing medium 2: NDM+1 μM RA (final concentration)

Differentiation-inducing medium 3: NDM+10 ng/mL PMA+1 μM RA (both final concentrations)

Differentiation-inducing medium 4: NDM only (by a known method)

The autonomic neural progenitor cells obtained by the above-described Step 5 were washed once with PBS, followed by addition of TrypLE Express Enzyme (250 μL/well), and cells were exfoliated by incubating the medium for five minutes. 10% FBS-containing DMEM was added to terminate the enzyme reaction, and the cells were collected in a centrifuge tube. After the medium was centrifuged at 200×g for four minutes, the supernatant was removed, cells were suspended with NDM, and the cells were counted. The cell concentrations were adjusted with the above-described differentiation-inducing media 1 to 4 (up to $2.5×10^5$ cells/cm$^2$), and cells were placed on the above-prepared 24-well plate coated with PLO/laminin at $5×10^5$ cells/well. Thereafter, culturing was continued while half of the medium was replaced with fresh differentiation-inducing media 1 to 4 twice per week. The media cultured for at least 20 days from the start of culturing with the differentiation-inducing media 1 to 4 were analyzed by immune staining and intracellular calcium imaging following the procedure described below.

3. Immune Cell Staining

The culture was washed with PBS and fixed with a 3.7% formaldehyde/PBS solution for 20 minutes. Then, the medium was washed with PBS, followed by addition of a 0.2% Tween 20/PBS solution, and the mixture was incubated for five minutes. Then, the 0.2% Tween 20/PBS solution was removed, and the plate was blocked for 30 minutes by adding a 4% Block Ace/0.2% Tween 20/PBS solution. Then, the plate was washed once with 0.2% Tween 20/PBS, followed by addition of a primary antibody/Can Get Signal Solution A (TOYOBO), and the mixture was left to stand overnight at 4° C. The used primary antibodies were as follows:

Anti-Tyrosine Hydroxylase (TH) antibody: 200-fold dilution

Anti-Choline Acetyltransferase (ChAT) antibody: 500-fold dilution

Anti-PHOX2B (mouse monoclonal) antibody: 100-fold dilution

Anti-PHOX2B (rabbit monoclonal) antibody: 100-fold dilution

Anti-MAP2 (mouse monoclonal) antibody: 500-fold dilution

The primary antibody solution was removed, and the plate was washed twice with 0.2% Tween 20/PBS, followed by addition of a secondary antibody/Can Get Signal Solution A (1000-fold diluted Alexa Fluro488 or 1000-fold diluted Alexa Fluor555) or 3000-fold diluted Hoechst 33342 solution, and the mixture was allowed to stand for one hour at room temperature. The secondary antibody solution was removed, and the plate was washed twice with 0.2% Tween 20/PBS and then observed under a fluorescence microscope.

The results are shown in FIGS. 2 to 8. FIG. 2 shows the results about cells subjected to differentiation induction to the 13th to 87th day from the start of culturing using the differentiation-inducing medium 4 (NDM only). The upper left figure shows stained TH, the upper right figure shows stained ChAT, the lower right figure shows an overlapped image of stained TH and ChAT, and the lower left figure shows a microscopic phase contrast image. A mixed state of cells positive for a sympathetic neuron marker TH and cells positive for a parasympathetic neuron marker ChAT was observed. The results showed that when differentiation was induced with NDM, autonomic neural progenitor cells were differentiation-induced into both sympathetic neurons and parasympathetic neurons.

FIG. 3 shows the results about cells subjected to differentiation induction to the 13th to 87th day from the start of culturing using the differentiation-inducing medium 1 (NDM+PMA). The upper left figure shows stained TH, the upper right figure shows stained ChAT, the lower right figure shows an overlapped image of stained TH and ChAT, and the lower left figure shows a microscopic phase contrast image. Both TH positive cells and ChAT positive cells were markedly reduced compared with FIG. 2. The result showed that addition of only PMA reduced the differentiation induction efficiency.

Figure 4:
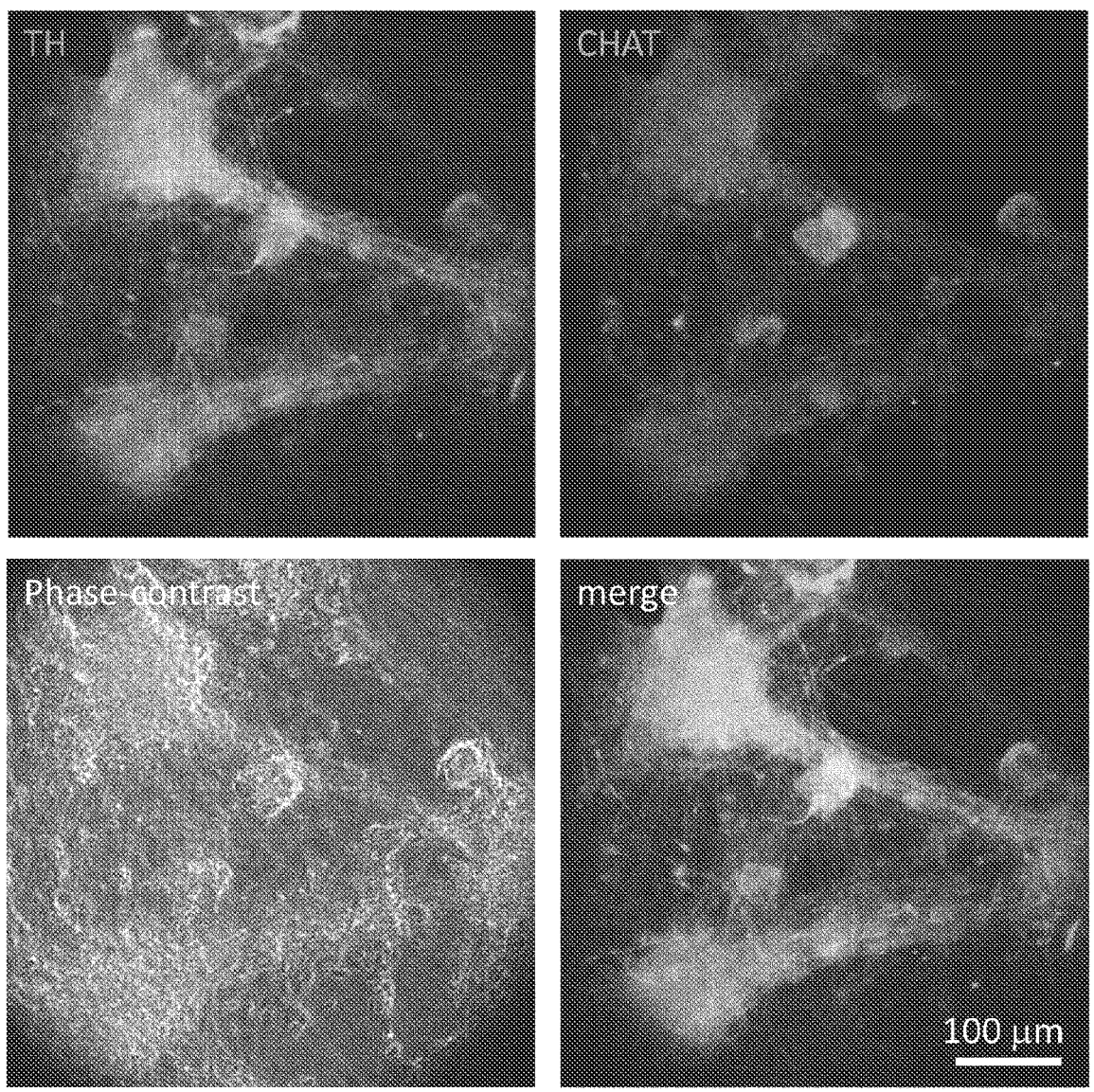
FIG. 4 is a diagram showing microscopic images of cells obtained by culturing in a differentiation-inducing medium 2 (NDM+RA) to the 13th to 87th day from the start of culture (upper left, stained TH; upper right, stained ChAT; lower right, an overlapped image of stained TH and ChAT; lower left, a microscopic phase contrast image).

FIG. 4 shows the results about cells subjected to differentiation induction to the 13th to 87th day from the start of culturing using the differentiation-inducing medium 2 (NDM+RA). The upper left figure shows stained TH, the upper right figure shows stained ChAT, the lower right figure shows an overlapped image of stained TH and ChAT, and the lower left figure shows a microscopic phase contrast image. No significant change was observed in the ratio of TH positive cells and ChAT positive cells compared with FIG. 2. The result showed that addition of only RA did not change the differentiation induction efficiency.

Figure 5:
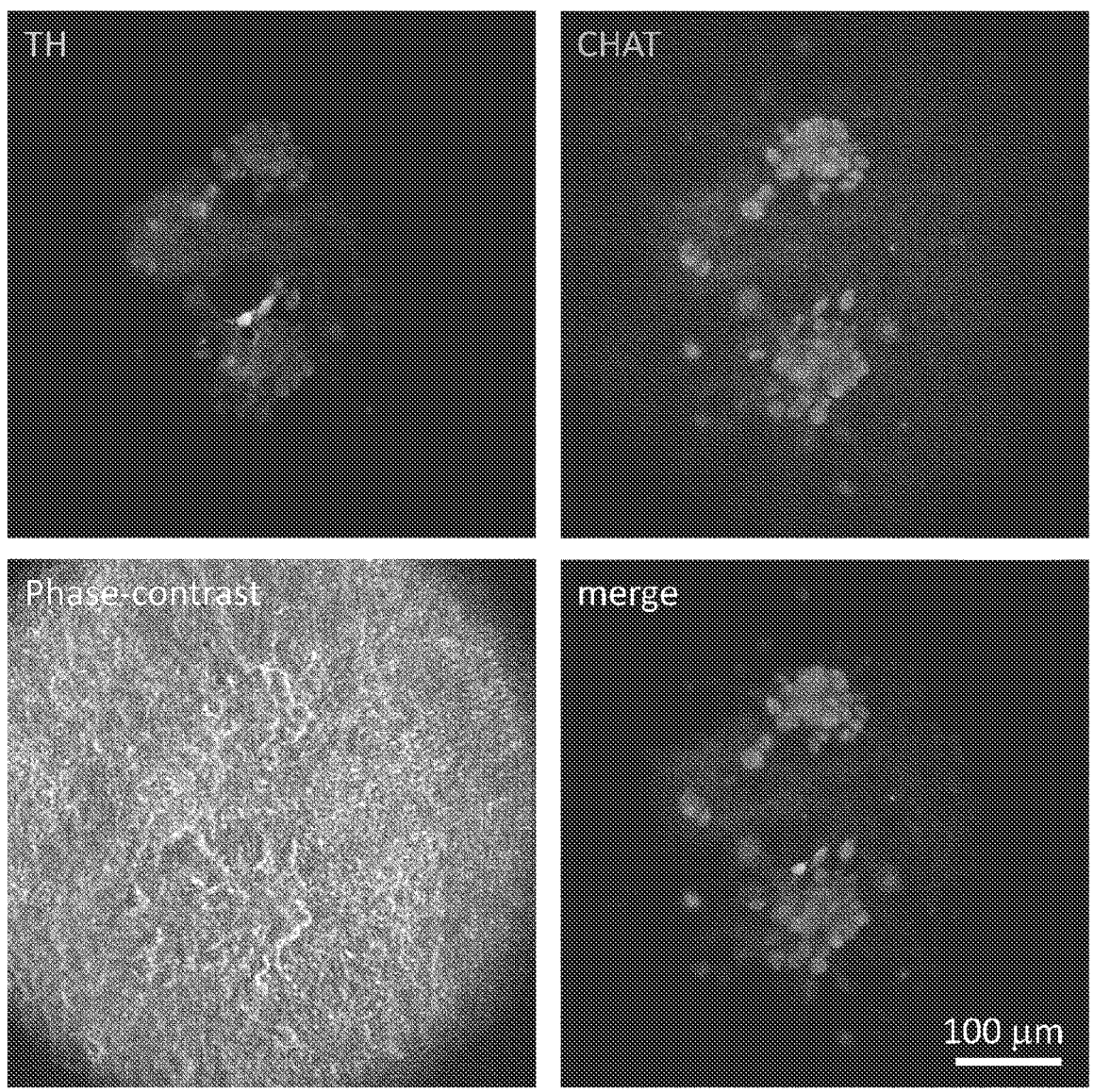
FIG. 5 is a diagram showing microscopic images of cells obtained by culturing in a differentiation-inducing medium 3 (NDM+PMA+RA) to the 13th to 87th day from the start of culture (upper left, stained TH; upper right, stained ChAT; lower right, an overlapped image of stained TH and ChAT; lower left, a microscopic phase contrast image).

FIG. 5 shows the results about cells subjected to differentiation induction to the 13th to 87th day from the start of culturing using the differentiation-inducing medium 3 (NDM+PMA+RA). The upper left figure shows stained TH, the upper right figure shows stained ChAT, the lower right figure shows an overlapped image of stained TH and ChAT, and the lower left figure shows a microscopic phase contrast image. Virtually no TH positive cells were observed, whereas a large number of ChAT positive cells were observed. The result showed that simultaneous addition of PMA and RA was important to induce selective differentiation into parasympathetic neurons.

Figure 6A:
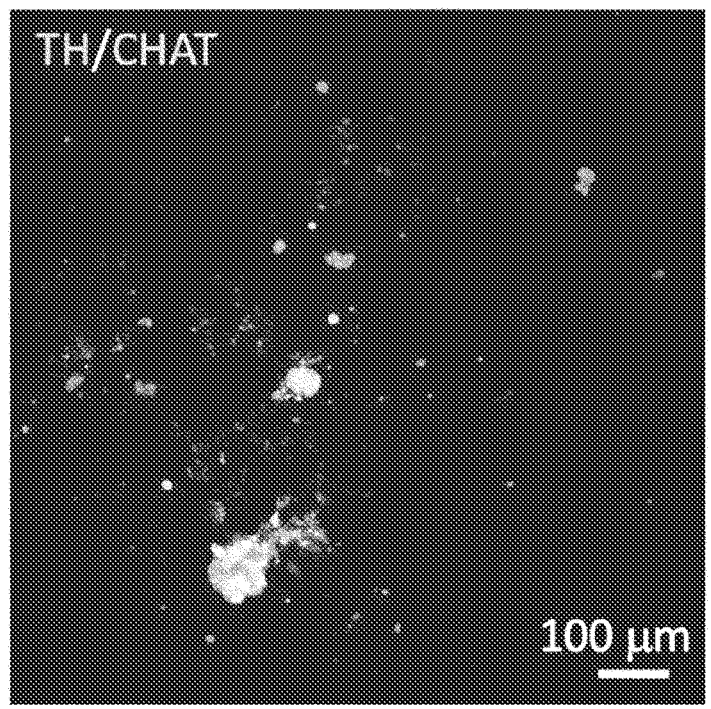
FIG. 6 is a diagram showing stained TH and ChAT in (A) cells obtained by culturing in the differentiation-inducing medium 4 (NDM only) to the 13th to 40th day from the start of culturing and (B) cells obtained by culturing in the differentiation-inducing medium 3 (NDM+PMA+RA) to the 13th to 44th day from the start of culturing in accordance with the known protocol shown in FIG. 1.
Figure 6B:
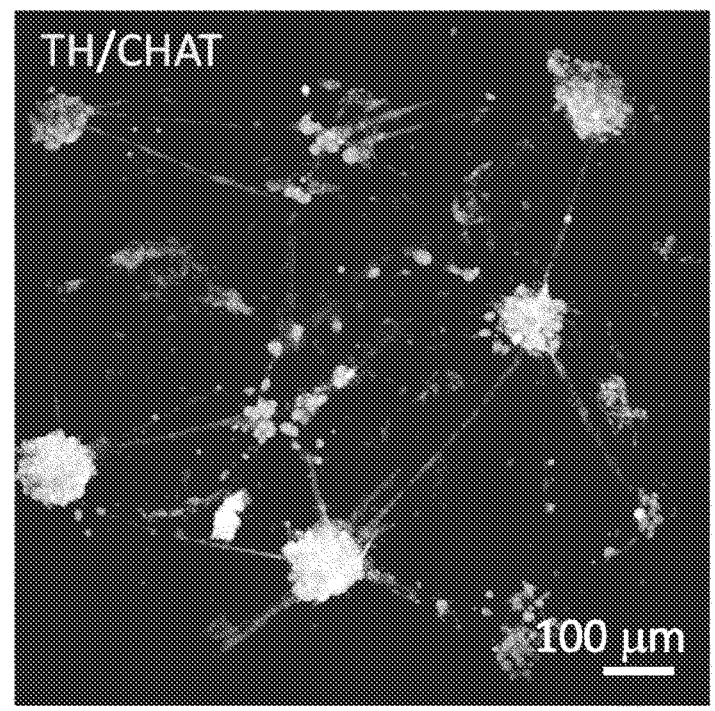
Figure 7:
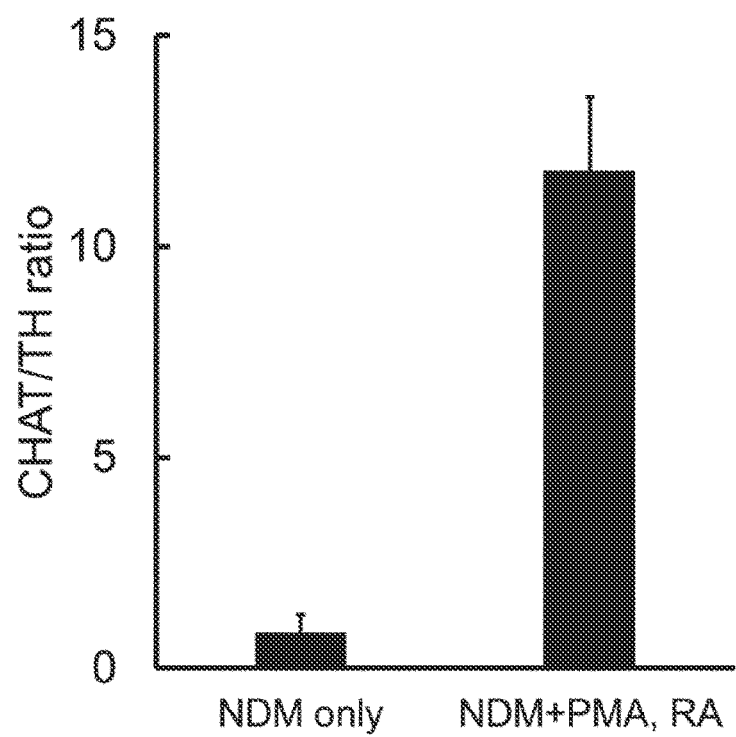
FIG. 7 is a graph comparing the results shown in FIG. 6, which were quantified.
Figure 8A:
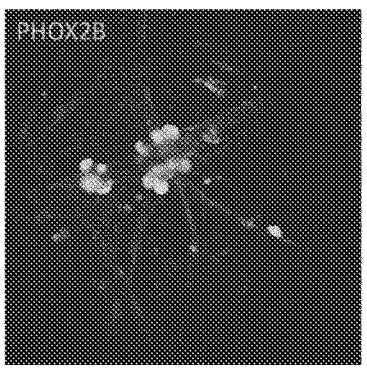
FIG. 8 is a diagram showing microscopic images of cells obtained by culturing in the differentiation-inducing medium 3 (NDM+PMA+RA) to the 13th to 87th day from the start of culturing (A, stained PHOX2B; B, stained ChAT; C, a microscopic phase contrast image; D, an overlapped image of stained PHOX2B and ChAT) and microscopic images of cells obtained by culturing in the differentiation-inducing medium 3 (NDM+PMA+RA) to the 13th to 38th day from the start of culturing (E, stained MAP2; F, stained PHOX2B; G, a microscopic phase contrast image; H, an overlapped image of stained AMP2 and PHOX2B).
Figure 8B:
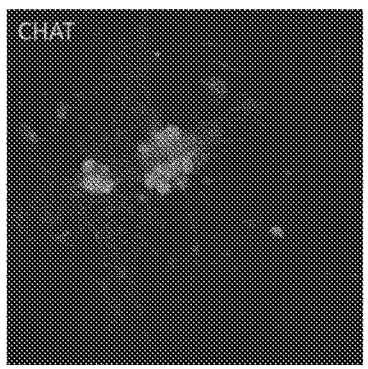
Figure 8C:
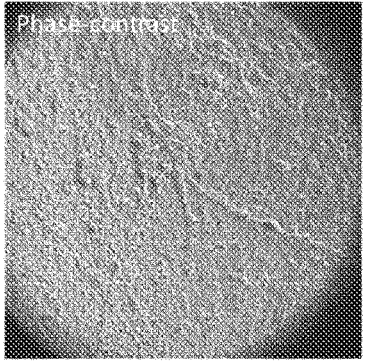
Figure 8D:
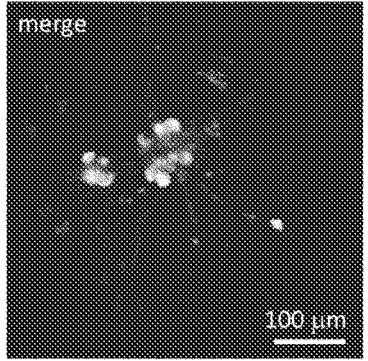
Figure 8E:
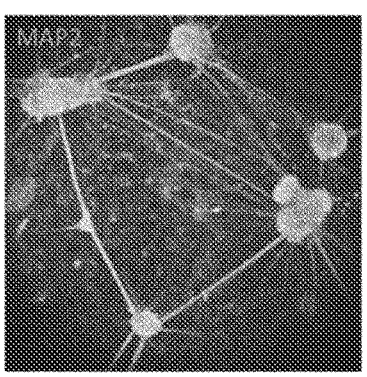
Figure 8F:
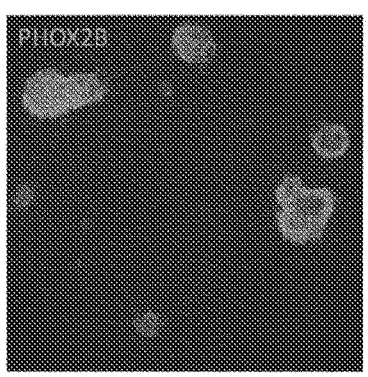
Figure 8G:
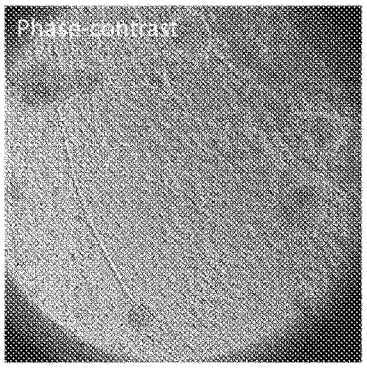
Figure 8H:
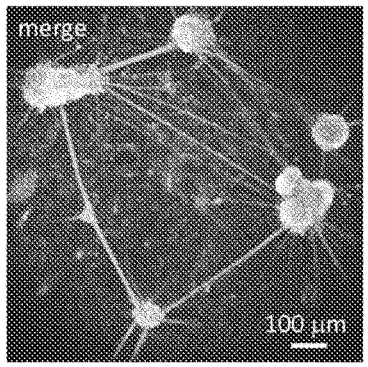

FIG. 6A shows the results about cells subjected to differentiation induction to the 13th to 40th day from the start of culturing using the differentiation-inducing medium 4 (NDM only). FIG. 6B shows the results of cells subjected to differentiation induction to the 13th to 44th day from the start of culturing using the differentiation-inducing medium 3 (NDM+PMA+RA). FIG. 7 shows the ratio of ChAT positive cells and TH positive cells (ChAT/TH) calculated by analyzing the results shown in FIG. 6 with ImageJ. When differentiation was induced with only NDM, ChAT positive cells and TH positive cells were mixed in about 1:1 ratio. In contrast, when differentiation was induced with NDM+PMA+RA, the number of ChAT positive cells was 10 times more than that of TH positive cells. The result demonstrated that autonomic neural progenitor cells could be induced to differentiate selectively into parasympathetic neurons by adding PMA and RA.

FIG. 8 shows stained PHOX2B, ChAT, and MAP2 for cells subjected to differentiation induction to the 13th to 87th day from the start of culturing (FIGS. 8A to 8D) or cells subjected to differentiation induction to the 13th to 38th day (FIGS. 8E to 8H), using the differentiation-inducing medium 3 (NDM+PMA+RA). ChAT positive cells were also positive for an autonomic neuron marker PHOX2B (FIGS. 8A to 8D). PHOX2B positive cells were also positive for a mature neuron marker MAP2 (FIGS. 8E to 8H). These results demonstrated that parasympathetic neurons could be selectively prepared using the differentiation-inducing medium 3 (NDM+PMA+RA).

4. Intracellular Calcium Imaging

Furthermore, response to nicotine stimulation for parasympathetic neurons obtained by culturing in the differentiation-inducing medium 3 (NDM+PMA+RA) was assessed by intracellular calcium imaging. 1 mg/mL Fluo-4 AM (Invitrogen, F14201)/DMSO was directly added to a medium on the differentiation induction culture 24th day at a final concentration of 5 µg/mL. After incubation in an incubator (37° C., 5% $CO_2$) for 30 minutes, the medium was removed and replaced with Ringer's solution (149 mM NaCl, 2.8 mM KCl, 2 mM $CaCl_2$, 1 mM $MgCl_2$, 10 mM HEPES, 10 mM D-(+)-glucose [pH 7.4]), and changes in the intracellular calcium concentrations were measured by detecting changes in the fluorescence intensity. For the measurement, 300 frames were photographed at a frame rate of 2 fps using an Olympus microscope (IX81), EMCCD (Andor iXon), and MetaMorph Software (Molecular Devices). Additionally, nicotine stimulation was performed by adding nicotine to Ringer's solution at a final concentration of 1 µM. ImageJ was used for data analysis after measurement.

Figure 9:
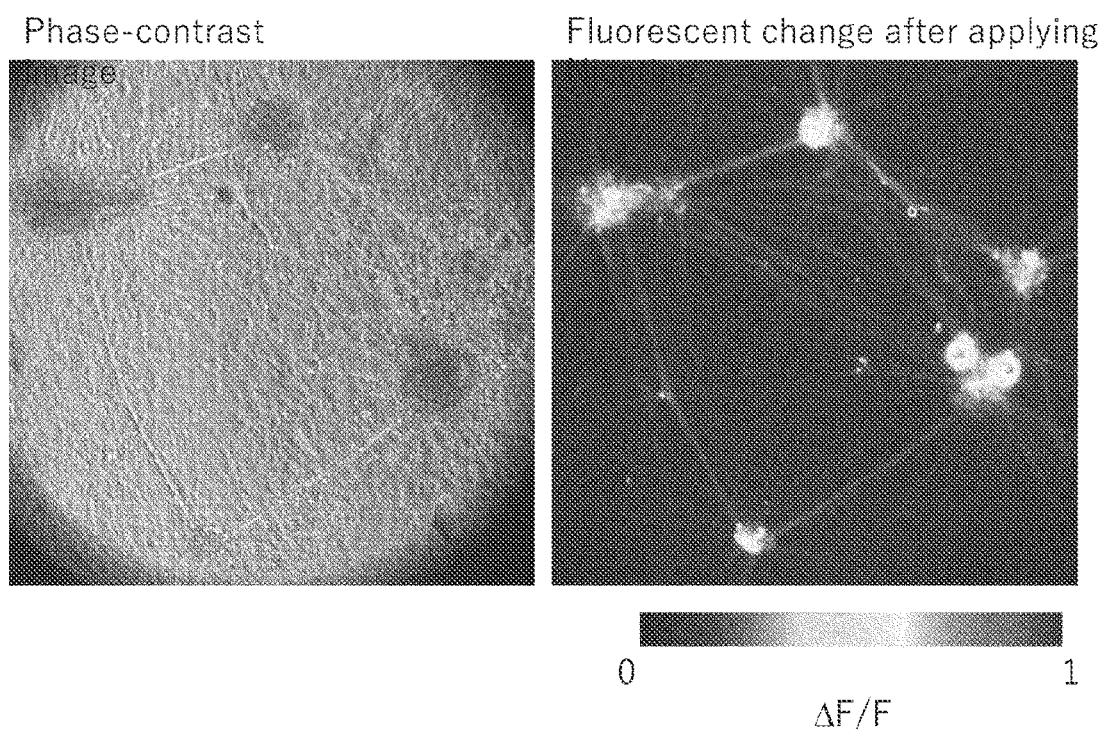
FIG. 9 is a diagram showing calcium imaging after nicotine stimulation of cells obtained by culturing in the differentiation-inducing medium 3 (NDM+PMA+RA) to the 13th to 37th day from the start of culturing (left, a microscopic phase contrast image; right, a fluorescence microscopy image).

The results are shown in FIG. 9. The neurons obtained by differentiation induction in the differentiation-inducing medium 3 (NDM+PMA+RA) to the 13th to 37th day from the start of culturing were demonstrated to show strong response to nicotine. This result showed that the prepared neurons had functional characteristics of autonomic neurons and supported, together with the above-described immune cell staining results, that the prepared neurons were parasympathetic neurons.

The invention claimed is:

1. A method for producing parasympathetic neurons from neural crest cells or autonomic neural progenitor cells derived therefrom, the method comprising:
    a step of culturing the neural crest cells or autonomic neural progenitor cells derived therefrom in the presence of a cAMP production promoter, a BDNF signaling pathway activator, a GDNF signaling pathway activator, an NGF signaling pathway activator, an NT-3 signaling pathway activator, vitamin C, a protein kinase C activator, and a retinoic acid receptor agonist,
    wherein the cAMP production promoter is selected from the group consisting of forskolin (FSK), L-858051, and dibutyryl cAMP (DB-cAMP),
    wherein the BDNF signaling pathway activator is brain-derived neurotrophic factor (BDNF),
    wherein the GDNF signaling pathway activator is glia cell line derived neurotrophic factor (GDNF),
    wherein the NGF signaling pathway activator is a nerve growth factor (NGF), and the NGF is NGF-β,
    wherein the NT-3 signaling pathway activator is neurotrophin-3 (NT-3),
    wherein the vitamin C is ascorbic acid,
    wherein the protein kinase C activator is phorbol 12-myristate 13-acetate (PMA), and
    wherein the retinoic acid receptor agonist is retinoic acid (RA).

2. The method according to claim 1, wherein the cAMP production promoter is forskolin.

3. The method according to claim 1, wherein the retinoic acid is all-transretinoic acid.

4. The method according to claim 1, the method further comprising
    a step of culturing the neural crest cells or autonomic neural progenitor cells derived therefrom in the presence of a BMP signaling pathway activator, an SHH signaling pathway inhibitor, and a Wnt signaling pathway inhibitor, before the step of culturing of claim 1,
    wherein the BMP signaling pathway activator is BMP2, BMP4, BMP7, or BMP2/4,
    wherein the SHH signaling pathway inhibitor is SANT-1, SANT-2, JK184, or jervine, and
    wherein the Wnt signaling pathway inhibitor is IWR-1, XAV939, or IWP-2.

5. The method according to claim 1, wherein the neural crest cells or autonomic neural progenitor cells derived therefrom are seeded at a concentration of $2 \times 10^5$ to $5 \times 10^5$ cells/cm$^2$.

6. The method according to claim 1, wherein the neural crest cells or autonomic neural progenitor cells derived therefrom are derived from a human.

7. The method according to claim 1, wherein the neural crest cells or autonomic neural progenitor cells derived therefrom are differentiated from pluripotent stem cells.

* * * * *

UNITED STATES PATENT AND TRADEMARK OFFICE
CERTIFICATE OF CORRECTION

PATENT NO. : 11,359,178 B2
APPLICATION NO. : 17/268234
DATED : June 14, 2022
INVENTOR(S) : Takayama et al.

It is certified that error appears in the above-identified patent and that said Letters Patent is hereby corrected as shown below:

In the Specification

Column 6, Line 38: Please correct "NGF-3" to read --NGF-β--

Column 8, Line 57: Please correct "LRPS/6" to read --LRP5/6--

Column 8, Line 60: Please correct "Ca'" to read --$Ca^{2+}$--

Column 8, Line 66: Please correct "LRPS/6" to read --LRP5/6--

Signed and Sealed this
Twentieth Day of December, 2022

Katherine Kelly Vidal
*Director of the United States Patent and Trademark Office*